United States Patent [19]
Bruce et al.

[11] Patent Number: 5,889,016
[45] Date of Patent: Mar. 30, 1999

[54] DIHYDROPYRIMIDONE DERIVATIVES AS NPY ANTAGONISTS

[75] Inventors: Marc A. Bruce, Wallingford; Graham S. Poindexter, Old Saybrook; Graham Johnson, Madison, all of Conn.

[73] Assignee: Bristol-Myers Squibb Company, Princeton, N.J.

[21] Appl. No.: 9,534

[22] Filed: Jan. 20, 1998

Related U.S. Application Data

[60] Provisional application Nos. 60/050,893 Jun. 26, 1997 and 60/037,183 Feb. 4, 1997.

[51] Int. Cl.$^6$ ........................ A61K 31/505; C07D 401/12
[52] U.S. Cl. ............................................. 514/274; 544/316
[58] Field of Search .............................. 544/316; 514/274

[56] References Cited

U.S. PATENT DOCUMENTS

| | | | |
|---|---|---|---|
| 4,707,486 | 11/1987 | Flockerzi et al. | 514/318 |
| 4,829,076 | 5/1989 | Szilágyi et al. | 514/356 |
| 4,912,119 | 3/1990 | Buschauer et al. | 514/333 |

FOREIGN PATENT DOCUMENTS

| | | |
|---|---|---|
| 533504 | 3/1993 | European Pat. Off. . |
| 534520 | 3/1993 | European Pat. Off. . |
| 2701480 | 2/1993 | France . |
| 4049-237-A | 6/1990 | Japan . |
| WO 96/14307 | 5/1996 | WIPO . |

OTHER PUBLICATIONS

C. Chaurasia, et al., "Nonpeptide Peptidomimetic Antagonists of thetide Y Receptor: Benextramine Analogs with Selectivity for the Perifpheral Y$_2$ Receptor", *J. Med. Chem.*, (1994) 37, 2242–2248.

M.B. Doughty, et al., "Neuropeptide Y (NPY) Functional Group Mimetics: Design, Synthesis, and Characterization as NPY Receptor Antagonists", *Bioorganic & Med. Chem. Lett.*, (1992) 2 (12), 1497–1502.

M.B. Doughty, C. S. Chaurasia and K. Li, "Benextramine–NeuorpeptidReceptor Interactions: Contributioenzylic Moieties to [$^3$H]Neuropeptide Y Displacement Activity", *J. Med. Chem.*, (1993) 36, 272–279.

L. Edvinsson, M. Adamsson and I. Jansen, "Neuropeptide Y Antagonistic Properties of D–Myl–Inositol–1.2.6–Trisphosphate in Guinea Pig Basilar Arteries", *Neuropeptides*, (1990) 17, 99–105.

H.M. Frankish, et al., "Neuropeptide Y, the Hypothalamus, and Diabetes: Insights into the Central Control of Metabolism", *Peptides*, (1995)16 (4), 757–771.

L. Grundemar and R. Hakånson, "Neuropeptide Y effector systems; perspectives for drug development", *TiPS*, (May, 1994) 15, 153–159.

J. Lehmann, "Neuropeptide Y: An Overview", *Drug. Dev. Res.*, (1990) 19, 329–351.

M.C. Michel, *TiPS*, "Receptors for neuropeptide Y: multiple subtypes and multiple second messengers", (Oct., 1991) 12, 389–394.

M.C. Michel and H.J. Motulsky,, "He 90481: A Competitive Nonpeptidergic Antagonist at Neuopeptide Y Receptors", *Annals. of the New York Acad. of Sci.*, (1990) 611, 392–394.

M.C. Michel and A. Buscher, "Neuropeptide Y and its antagonists", *Drugs of the Future*, (1992) 17 (1), 39–45.

K. Rudolf, et al., "The first highly potent and selective non-peptide neuropeptide Y Y$_1$ receptor antagonist: BIBP3226", *Eur. J. Pharmacology*, (1994) 271, R11–R13.

C. Serradeil–LeGal, et al., "SR120107A and SR120819A: Two Potent and Selective, Orally–Effective Antagonists for NPY Y$_1$ Recptors", *Society for Neuroscience*, (1994) Abstract No. 376.14.

*Primary Examiner*—John M. Ford
*Attorney, Agent, or Firm*—Aldo A. Algieri

[57] ABSTRACT

The present invention provides a series of non-peptidergic antagonists of NPY comprising piperidine derivatives of 4-phenyl-1,4-dihydropyrimidinones of the Formula I

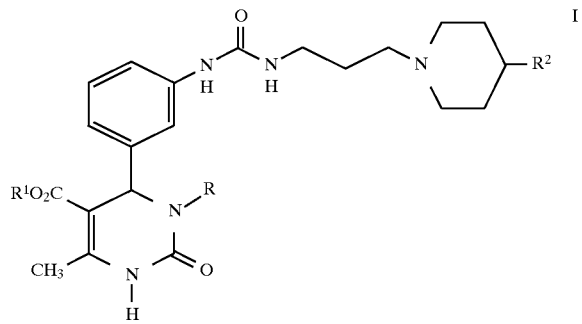

wherein R, R$^1$ and R$^2$ are defined herein. As antagonists of NPY-induced feeding behavior, these compounds are expected to act as effective anorexiant agents in promoting weight loss and treating eating disorders.

7 Claims, No Drawings

DIHYDROPYRIMIDONE DERIVATIVES AS NPY ANTAGONISTS

CROSS-REFERENCE TO RELATED APPLICATION

This nonprovisional application claims the benefit of copending provisional applications, U.S. Ser. No. 60/050,893, filed Jun. 26, 1997, and U.S. Ser. No. 60/037,183 filed Feb. 4, 1997.

FIELD OF THE INVENTION

The present invention provides novel heterocyclic carbon compounds comprising 4-phenyl-1,4-dihydropyrimidinones with a piperidinyl containing moiety attached to the 3-position of the 4-phenyl ring. These compounds act as NPY antagonists.

BACKGROUND OF THE INVENTION

Neuropeptide Y (NPY) is a 36 amino acid peptide first isolated in 1982 from porcine brain [K. Takemoto, *Proc. Nat. Acad. Sci.*, (1982) 79, 5485–5489; D. R. Gehlert, *Life Sciences*, (1994) 55, 551–62; L. Grundemar and R. Hakanson, *TIPS*, (1994) 15, 153–159; J. M. Lundberg, *TIPS*, (1996) 17, 301–304; C. Wahlestedt and D. J. Reis, *Ann. Rev. Pharmacol. Toxicol.*, (1993) 32, 309–352; P. A. Hipskind, *Ann. Rep. Med. Chem.*, (1996), 31,1–10; J. D. White, *Regulatory Peptides*, (1993) 49, 93–107; A. Sahu and S. P. Kalra, *Trends Endocrinol. Metab.*, (1993) 4, 217–224; Y. Dumont, J.-C. Martel, A. Fournier, S. St. Pierre and R. Quirion, *Prog. Neurobiol.*, (1992) 38, 125–167; M. C. Michel and A. Buscher, *Drugs of the Future*, (1992) 17, 39–45; M. C. Michel, *TIPS*, (1991) 12, 389–394; J. Lehmann, *Drug. Dev. Res.*, (1990) 19, 329–351; G. Williams, *Peptides*, (1995) 4, 757–771]. The peptide is a member of a larger peptide family which also includes peptide YY (PYY), pancreatic peptide (PP), and the non-mammalian fish pancreatic peptide Y (PY). Neuropeptide Y is very highly conserved in a variety of animal, reptile and fish species. It is found in many central and peripheral sympathetic neurons and is the most abundant peptide observed in the mammalian brain. In the brain, NPY is found most abundantly in limbic regions. The peptide has been found to elicit a number of physiological responses including appetite stimulation, anxiolysis, hypertension, and the regulation of coronary tone.

Structure-activity studies with a variety of peptide analogs (fragments, alanine replacements, point mutations, and internal deletion/cyclized derivatives) suggest a number of receptor subtypes exist for NPY [L. Grundemar and R. Hakanson, *TiPS*, (1994) 15, 153–159]. These currently include the $Y_1$, $Y_1$-like, $Y_2$, $Y_3$, and the $Y_4$ subtypes.

Although specific peptidic antagonists have been identified for most of the subtypes, few selective non-peptidic antagonists have been reported to date. Several competitive but non-selective, non-peptidic antagonists are known. The heterocyclic guanidine derivative He 90481 (4) was found to be a weak but competitive antagonist of NPY-induced Ca++ entry in HEL cells ($pA_2$=4.43) [M. C. Michel and H. J. Motulsky, *Annu. Rev. N.Y. Acad. Sci.*, (1990) 611, 392–394; U.S. Pat. No. 4,912,119, 1990 (Heumann Pharma GMBH)]. The compound was also found to have $\alpha_2$-adrenergic and histaminergic activity at this dose range. D-Myo-inositol-1, 2,6-triphosphate (5) was reported to be a potent but non-competitive antagonist to NPY-induced contractions in guinea pig basilar artery [L. Edvinsson, M. Adamsson and I. Jansen, *Neuropeptides*, (1990) 17, 99–105]. Similarly, the benextramine-like bisguanidines 6a and 6b were reported to displace $^3$H-NPY in rat brain ($IC_{50}$, 19 and 18.4 $\mu$M) and to display functional antagonism in rat femoral artery [M. B. Doughty, C. Chaurasia and K. Li, *J. Med. Chem.*, (1993) 36, 272–79; M. B. Doughty, S. S. Chu, G. A. Misse and R. Tessel, *BioMed. Chem. Lett.*, (1992) 2, 1497–1502; C. Chaurasia, G. Misse, R. Tessel and M. B. Doughty, *J. Med. Chem.*, (1994) 37, 2242–48]. The bisguanidine 6b was shown to be functionally selective for the $Y_2$ receptor since it antagonized the effect of the $NPY_2$ agonist $NPY_{13-36}$ but had no effect on the vasoconstrictive activity of the $NPY_1$ agonist [Leu31, Pro34]NPY [C. Chaurasia, G. Misse, R. Tessel and M. B. Doughty, *J. Med. Chem.*, (1994) 37, 2242–48].

A substantial body of art has accumulated over the past two decades with respect to 4-aryl-1,4-dihydropyridine compounds. A large number of these possess calcium antagonist properties and find utility in the treatment of cardiovascular diseases. Several 4-aryl-1,4-dihydropyridines with piperidine-ring-containing-substituents have been reported.

A series of compounds of formula (1) was claimed to be

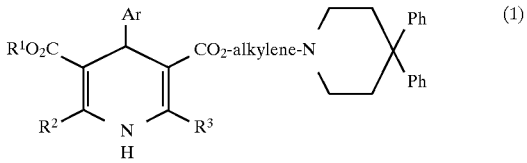

useful as vasodilators, antihypertensives and diuretics in U.S. Pat. No. 4,707,486.

A series of dihydropyridines, including compounds of formula (2), were disclosed and claimed to have antitumor promoting activity in European Patent Application 533,504.

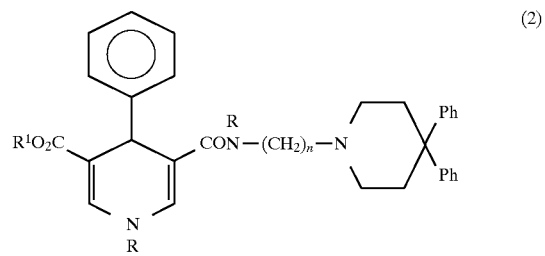

European Patent Application 534,520 discloses related compounds having formula (3) wherein $R_5$ is alkyl, phenyl and aralkyl.

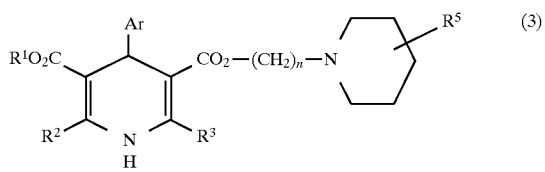

A compound of formula (4) has been disclosed in JO 4049-237-A and claimed to be an inhibitor of Phospholipase $A_2$.

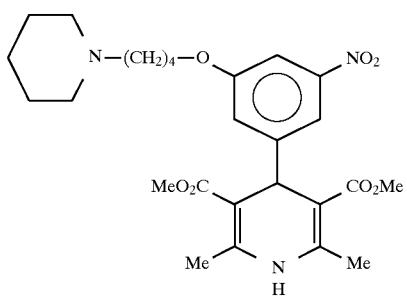
(4)

Of less significance is a series of antihypertensive dihydropyridine anilide derivatives disclosed in U.S. Pat. No. 4,829,076 and containing compounds of formula (5)

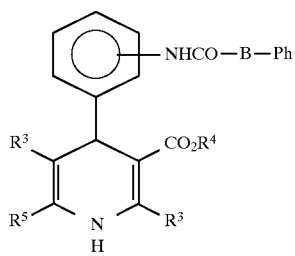
(5)

in which B is a chemical bond or an alkylene group.

Dipeptide-like sulfonamidoyl amidine derivatives of formula (6)

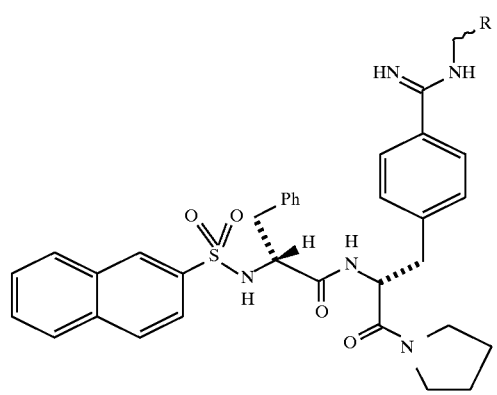
(6)

R =

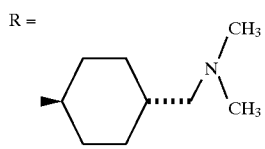

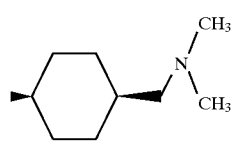

have been disclosed as selective NPY $Y_1$ antagonists. See: French Patent 9,301,686; Serradeil-LeGal, et al., *Society for Neuroscience*, (1994) abstract no. 376.14.

A guanidine derivative of formula (7) having NPY $Y_1$ selective receptor antagonist activity was

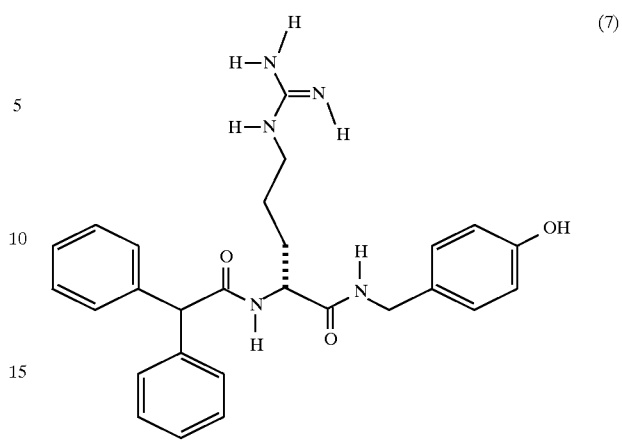
(7)

disclosed by Rudolf, et al., *Eur. J. Pharmacology*, (1994) 271, R11-13.

A series of substituted benzylamine derivatives of the general formula (8) having NPY $Y_1$ receptor antagonist activity

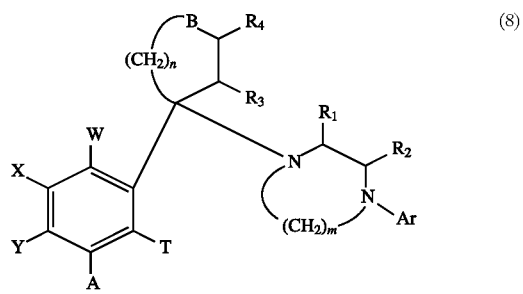
(8)

was disclosed by Peterson, et al. in International Patent Application WO 96/14307, published May 17, 1996.

These reference compounds are readily distinguished structurally from the compounds of the instant invention by virtue of many of the art compounds having the piperidine substituents attached to the dihydropyridine ring itself as well as by the nature of most of the linking functional groups, e.g. oxyalkylenyl and carboxylate groups. In contrast, compounds of the instant invention contain an alkylenylpiperidine moiety attached to the 3-position of the 4-phenyl ring by means of an urea connection. Not only are the present compounds structurally novel, they also have been discovered to possess novel NPY antagonist activity.

In summary, the prior art does not disclose nor suggest the unique combination of structural fragments which embody these novel dihydropyrimidinone derivatives as having good antagonist activity at NPY $Y_1$ receptor sites.

SUMMARY AND DETAILED DESCRIPTION OF THE INVENTION

The present invention comprises the compounds of Formula I,

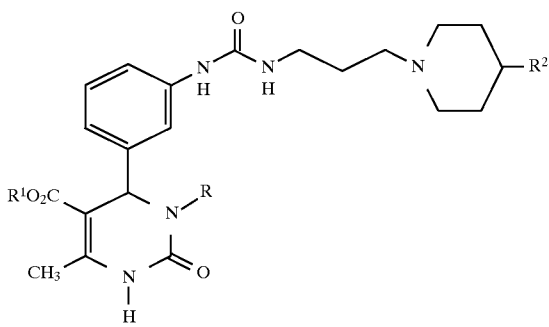

The term "$C_{1-3}$ alkyl" indicates that the alkyl group contains from one to three carbon atoms, such as methyl, ethyl, propyl and isopropyl. Preferred compounds of the instant invention are Formula I compounds wherein R is —$CO_2R^1$ and $R^1$ is methyl. Most preferred compounds are those wherein $R^2$ is selected from substituted phenyl, particularly with methoxy substituents.

The compounds of the present invention can exist as optical isomers and both the racemic mixtures of these isomers as well as the individual optical isomers themselves are within the scope of the present invention. The racemic mixtures can be separated into their individual isomers through well known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, dichloroacetic acid, tartaric acid, lactic acid, succinic acid, citric acid, maleic acid, fumaric acid, sorbic acid, aconitic acid, salicylic acid, phthalic acid, enanthic acid, and the like.

The Formula I compounds can also be quaternized by standard techniques to yield quaternary piperidinium salt products of Formula I. Quaternization would be expected to maximize the peripheral effects of Formula I compounds and minimize brain penetration.

The compounds of the present invention may be prepared by various procedures such as those illustrated herein in the examples, in the reaction schemes and variations thereof which would be evident to those skilled in the art. The various compounds of Formula I may advantageously be prepared from the dihydropyrimidinone intermediates Va, Vb and Vc as illustrated in Reaction Schemes 2 and 3.

The various dihydropyrimidinone intermediates are generally prepared from the Knoevenagel adduct of Formula II as illustrated in Reaction Scheme 1.

SCHEME 1

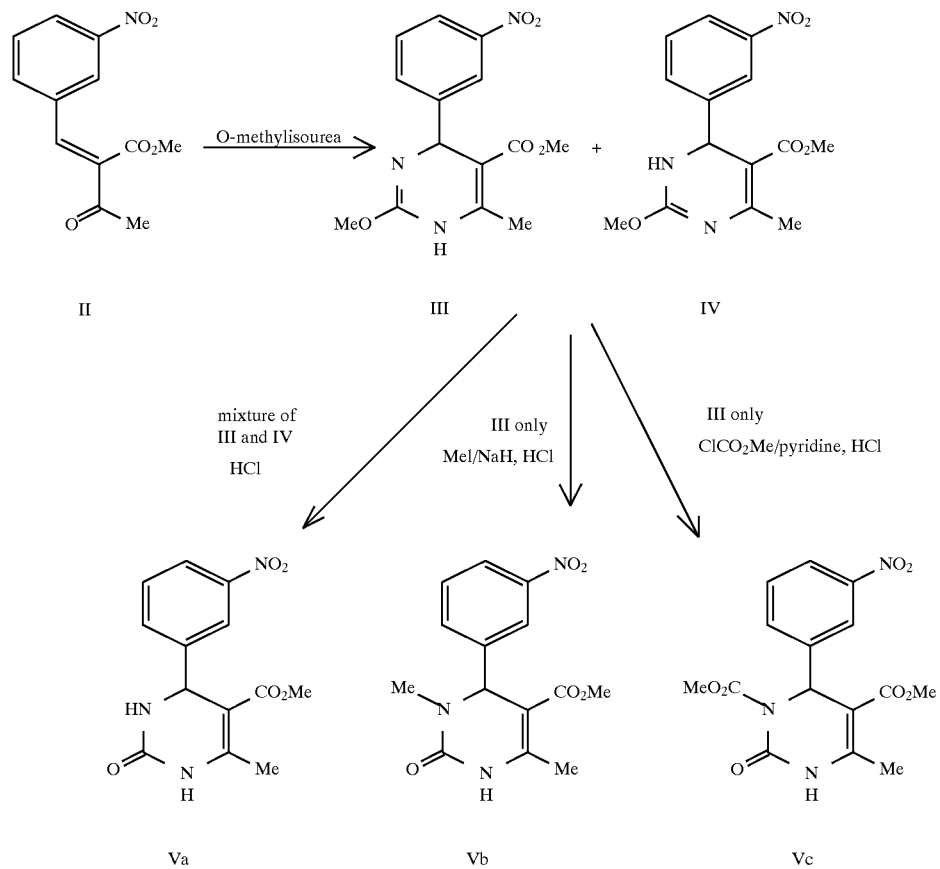

It will be appreciated by those skilled in the art that the reaction of the intermediate of Formula II with O-methylisourea produced a mixture of methoxypyrimidine isomers of Formulas III and IV. Advantageously, the methoxypyrimidine isomer of Formula III may selectively be crystallized from the mixture of isomers by the method described herein. The resulting filtrate that contains a residual mixture of isomers of Formulas III and IV may readily be hydrolyzed under acidic conditions in aqueous tetrahydrofuran to provide the 2-oxopyrimidine intermediate of Formula Va.

The intermediates of Formulas Vb and Vc are advantageously prepared from the single methoxypyrimidine compound of Formula III by alkylation and acylation reactions, respectively. The alkylation of the compound of Formula III with a lower alkyl alkylating agent such as methyl iodide in an inert organic solvent followed by acid hydrolysis of the methoxy group afforded the intermediate of Formula Vb. The acylation of the compound of Formula III with a lower alkyl ester of chloroformate in the presence of about one equivalent of a base such as pyridine, lutidine, triethylamine and the like in an inert organic solvent then followed by acid hydrolysis of the methoxy group afforded the intermediate of Formula Vc.

The compounds of Formula I were prepared from the intermediates of Formulas Va, Vb and Vc as outlined by the process in Reaction Scheme 2 or the alternate process as outlined in Scheme 3. In Reaction Scheme 2, the nitrophenyl intermediates of Formulas Va, Vb and Vc were subjected to catalytic hyrdrogenation in an acetic acid solvent to produce the aminophenyl intermediates of Formulas VIa, VIb and VIc which were then coupled with the activated carboxylate intermediate of Formula VII to produce the corresponding dihydropyrimidinone compounds of Formula Ia, Ib and Ic. It should be understood that the intermediate of Formula VII can readily be prepared by methods described in the literature and preferably by the method described herein.

SCHEME 2

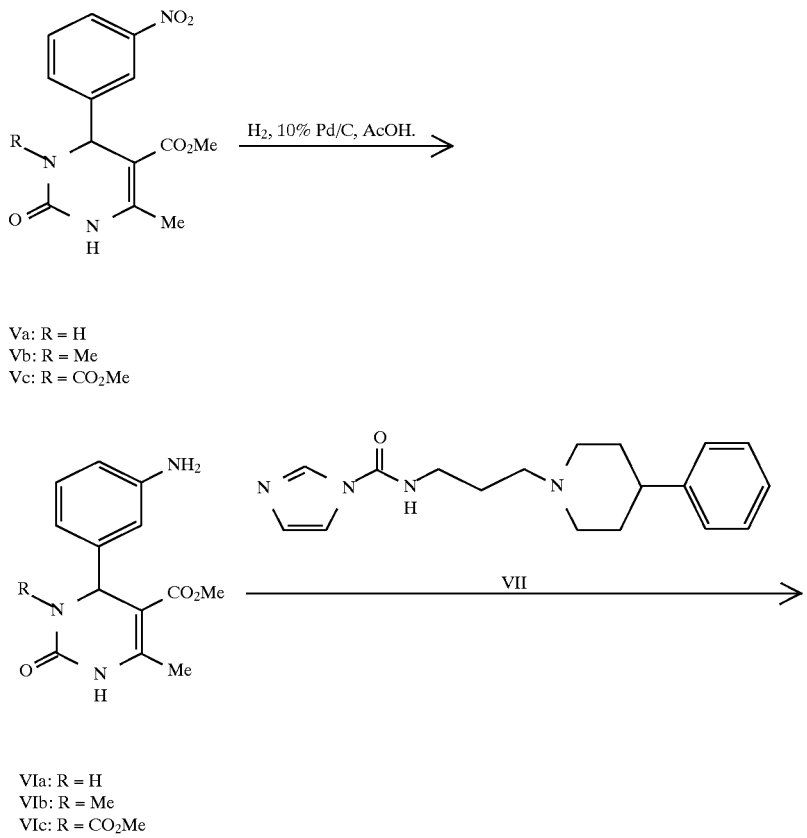

-continued
SCHEME 2
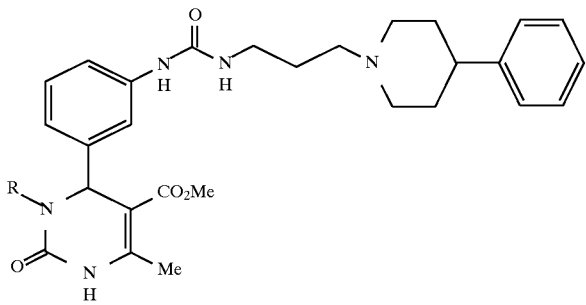
Ia: R = H
Ib: R = Me
Ic: R = CO₂Me
SCHEME 3
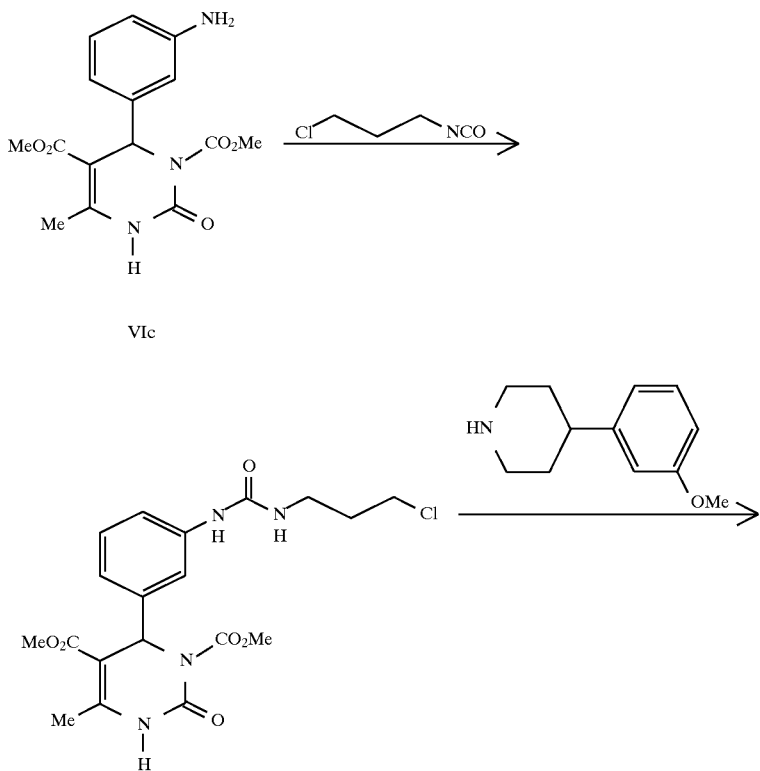

-continued
SCHEME 3

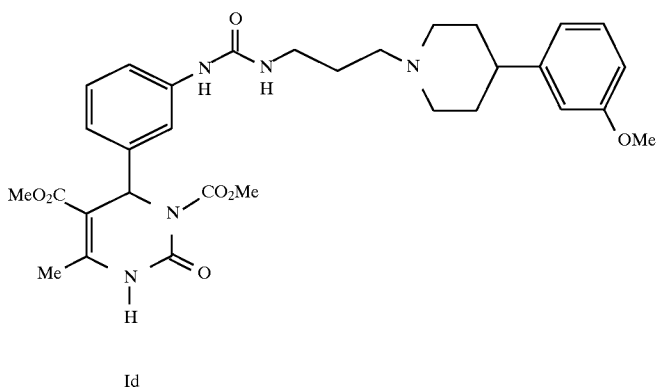

Id

In an alternate process, the preparation of the dihydropyrimidinone compound of Formula Id is illustrated in Reaction Scheme 3. An aminophenyl compound of Formula VIc is first treated with 3-chloropropyl isocyanate to produce a urea intermediate of Formula VIII which is then used to alkylate 4-(3-methoxyphenyl)-piperidine with sodium iodide as catalyst under basic conditions in an inert solvent to afford the compound of Formula Id.

Additional reactions intermediates and Formula I products can be prepared by appropriate modification of the foregoing synthetic schemes and procedures. Such modifications would be obvious to those skilled in the art.

The compounds of this invention demonstrate binding affinity at NPY $Y_1$ receptors. This pharmacologic activity is assayed in SK-N-MC (human neuroblastoma) cell membranes using iodine-125-labeled I-PYY as a radioligand. The compounds of this invention had good binding affinities as evidenced by $IC_{50}$ values being about 1 $\mu$M or less at NPY $Y_1$ receptors. Preferred compounds have $IC_{50}$ values less than 100 nM.

Although as a class, these types of compounds have significant affinity for $\alpha_1$-adrenergic receptors and/or $Ca^{++}$ channels, the compounds of this invention possess much weaker affinities for $\alpha_1$ adrenergic receptors and $Ca^{++}$ channels. Pharmacologically, these compounds act as selective NPY antagonists at NPY $Y_1$ receptor sites. As such, the compounds of Formula (I) are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula (I) or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:
disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal track;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and disorders, such as male erectile dysfunction and benign prostatic hyperplasia, and reproductive disorders;

conditions or disorders associated with inflammation;

respiratory diseases, such as asthma and conditions related to asthma and bronchoconstriction;

diseases related to abnormal homone release, such as leutinizing hormone, growth hormone, insulin and prolactin;

sleep disturbance and diabetes.

There is evidence that NPY contributes to certain symptoms in these disorders: hypertension, eating disorders, and depression/anxiety [C. Wahlestedt and D. J. Reis, *Annual Rev. Pharmacol. Toxicol.*, (1993) 32, 309–52; p. 331]; as well as circadian rhythms. Compounds of this invention are expected to be useful in treating these disorders as well as sleep disturbance and diabetes.

These compounds are expected to block NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a Formula I compound or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 20 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat hypertension, depression, diabetes and anxiety disorders.

Therapeutically, the instant compounds are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethelene glycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C when not specified.

The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), singlet (s), multiplet (m), doublet (d), triplet (t) doublet of doublets (dd), quartet (q) or pentuplet (p). Abbreviations employed are DMSO-$d_6$, (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were generally employed using potassium bromide (KBr) as diluent. The elemental analyses are reported as percent by weight.

General Method for the Preparation of Intermediate VII

STEP A. 3-(4-Phenyl-1-piperidinyl)propanenitrile

A mixture of 4-phenylpiperidine (23.5 g, 146 mmol) and acrylonitrile (12.0 mL, 180 mmol) in MeCN (150 mL) was refluxed for 4 h, and then the solvent removed in vacuo. The residue was partitioned between CH$_2$Cl$_2$ (200 mL) and H$_2$O (100 mL), the organic extract was dried over Na$_2$SO$_4$, and the solvent removed in vacuo to yield an amber oil (32.7 g, quantitative yield): $^1$H NMR (DMSO-$d_6$) $\delta$ 7.25 (m, 5 H), 2.96 (d,2 H, J=11.4 Hz), 2.67 (t,2 H, J=7.5 Hz), 2.58 (t,2 H, J=7.5 Hz), 2.48(m, 1 H), 2.06(t,2 H, J=12.0 Hz), 1.70(m,2 H), 1.64(t,2 H, J=12.0 Hz); $^{13}$C NMR (DMSO-$d_6$) $\delta$ 146.1, 128.3, 126.7, 126.0, 120.1, 53.2, 41.7, 33.0, 15.1.

Anal. Calcd for C$_{14}$H$_{18}$N$_2$. 0.2H$_2$O : C, 77.17; H, 8.51; N, 12.86. Found: C, 77.13; H, 7.95; N, 12.65

STEP B. 1-(3-Aminopropyl)-4-phenylpiperidine

A solution of the compound of Step A (31 g, 140 mmol) in MeOH (170 mL) and 30% aqueous NH$_3$ (30 mL) containing Raney nickel was shaken in a Parr apparatus under H$_2$ (50 psi) for 1 h. The catalyst was then removed by filtration over Celite, and the solvent removed in vacuo to yield a light yellow paste (31.5 g, quantitative yield) [Wade, P. C.; and Vogt, R., U.S. Pat. No. 3,995,045,1976].

STEP C. 1-[[[3-(4-Phenyl-1-piperidinyl)propyl]amino]-carbonyl]imidazole (VII)

To a stirred solution of 1,1'-carbonyidiimidazole (CDl, 15 g, 92 mmol) in MeCN (200 mL) at 0° C. under N$_2$ was added dropwise a solution of the compound of Step B (10 g, 46 mmol) in $CH_2Cl_2$ (100 mL) over 30 min. The resulting mixture was stirred an additional 30 min at 0° C., then for 30 min at room temperature. The reaction was quenched with $H_2O$ (100 ml), and the resulting mixture was extracted with ether (200 mL). The organic extract was washed with $H_2O$ (2×100 mL), followed by brine (100 mL), and dried over $Na_2SO_4$. The solvent was removed in vacuo to afford a light amber oil of the intermediate of Formula VII (12.3 g, 85% yield): $^1$H NMR (CDCl$_3$) δ 8.90 (s, 1 H), 8.18 (s, 1 H), 7.41 (s, 1 H), 7.31 (m, 2 H), 7.21 (m, 3 H), 7.10 (s, 1 H), 3.54 (m, 2 H), 3.14 (d,2 H, J=11.7 Hz),2.60(t, 2 H, J=5.4 Hz), 2.07 (t,2 H, J=12.0 Hz), 1.08 (m, 6 H); $^{13}$C NMR (CDCl$_3$) δ 149.0, 145.5, 136.2, 130.4, 128.6, 126.7, 126.4, 115.8, 59.1, 54.6, 42.4, 33.4, 23.5.

Anal. Calcd for $C_{18}H_{24}N_4O$. 0.9 $H_2O$: C, 65.79; H, 7.91; N, 17.05. Found: C, 66.13; H, 7.62; N, 16.83.

EXAMPLE 1

1,2,3,4-Tetrahydro-6-methyl-4-(3-nitrophenyl)-2-oxo-5-pyrimidinecarboxylic acid, methyl ester Following the general method described by O'Reilly, B. C.; and Atwal, K. S. *Heterocycles*, (1987) 26, 1185, a mixture of the compound of Formula II [prepared by the method described by Jones, *G. Org. Reactions*, (1967) 15, 204] (20 g, 80 mmol), O-methylisourea. $H_2SO_4$ (17.2 g, 100 mmol) and $NaHCO_3$ (25 g, 300 mmol) in DMF (200 mL) was stirred at room temperature for 1 h, and then heated overnight at 65° C. The mixture was cooled, and then partitioned between EtOAc (2×400 mL) and $H_2O$ (400 mL). The organic extracts were combined and rinsed with $H_2O$ (2×200 mL), followed by brine (200 mL), and the solvent was removed in vacuo. The identities of the resulting methoxypyrimidine isomers were determined by $^1$H NMR. A white solid (2.67 g, compound III) was isolated from $Et_2O$ containing a small amount of MeOH. Upon standing, the mother liquor produced a second crop of white solid (2.68 g, compound IV). Subsequent crops (4.05 g) contained a mixture of compound III and IV, for a combined yield of 59%. Due to the apparent instability of the methoxypyrimidines, full characterization was not obtained, and these compounds were used promptly in subsequent reactions.

A mixture of compound III and IV (5.0 g, 16 mmol) in MeOH:THF 1:1 (100 mL) and 3N HCl (30 mL) was stirred overnight, resulting in the formation of a white precipitate. The solvent was removed in vacuo, and the residue triturated in 100% EtOH to produce the title compound Va as a white solid (3.42 g, 72% yield): mp 268°–269° C.; $^1$H NMR (DMSO-d$_6$) δ 9.40 (s, 1 H), 8.13 (d, 1 H, J=7.5 Hz), 8.08 (s, 1 H), 7.93 (s,1 H), 7.66 (m, 2 H), 5.29 (d, 1 H, J=3.3 Hz), 3.53 (s, 3 H), 2.27 (s, 3 H); $^{13}$C NMR (DMSO-d$_6$) δ 165.6, 151.8, 149.7, 147.9, 146.8, 132.9, 130.3, 122.4, 120.9, 98.1, 53.4, 50.9, 17.9.

Anal. Calcd for $C_{13}H_{13}N_3O_5$. 0.2$H_2O$. 0.1 $C_2H_6O$: C, 52.94; H, 4.71; N, 14.03. Found: C, 53.03; H, 4.64; N, 13.73.

EXAMPLE 2

4-(3-Aminophenyl)-1,2,3,4-tetrahydro-6-methyl-2-oxo-5-pyrimidinecarboxylic acid, methyl ester A solution of the compound of Example I in AcOH containing 10% Pd/C and was shaken in a Parr apparatus under $H_2$ (50 psi) for about 1 h. The catalyst was removed by filtration over Celite and the solvent was removed in vacuo to afford the title compound as a light yellow solid (98% yield): mp 222°–234° C.; $^1$H NMR (DMSO-d$_6$) δ 9.12 (s, 1 H), 7.63 (s, 1 H), 6.92 (t, 1 H, J=7.5 Hz), 6.40 (m, 3 H), 5.04 (s, 2 H), 4.98 (d, 1 H, J=3.3 Hz), 3.52 (s, 3 H), 2.22 (s, 3 H); $^{13}$C NMR (DMSO-d$_6$) δ 166.0, 152.2, 148.7, 148.1, 145.3, 128.8, 113.8, 112.9, 111.6, 99.2, 54.0, 50.7, 17.8.

Anal. Calcd for $C_{13}H_{15}N_3O_3$. 0.25 $H_2O$: C, 58.75; H, 5.89; N, 15.81. Found: C, 59.12; H, 5.76; N, 15.39.

EXAMPLE 3

1,2,3,4-Tetrahydro-6-methyl-2-oxo-4-[3-[[[[3-(4-phenyl-1-piperidinyl) propyl]amino]carbonyl]amino]phenyl]-5-pyrimidinecarboxylic acid, methyl ester hydrochloride A mixture of the compound of Example 2 and the intermediate of Formula VII in MeCN was refluxed overnight. After the solvent was removed in vacuo from the reaction mixture, the residue was partitioned between 1N HCl (50 mL) and $CH_2Cl_2$:MeOH 3:1 (6×50 ML). The organic extracts were combined, made basic with saturated $Na_2CO_3$, dried over $Na_2SO_4$, and the solvent was removed in vacuo. Flash chromatography (SiO$_2$: MeOH/CH$_2$Cl$_2$) yielded a residue of 700 mg, which was dissolved in MeOH and combined with 1N HCl/Et$_2$O (1.5 mL). The solvent was removed in vacuo, and the residue triturated in acetone to afford the title compound as a pale yellow solid (455 mg, 12% yield): mp 170°–178° C. (with decomposition); $^1$H NMR (DMSO-d$_6$) δ 10.44 (br s, 1 H), 9.19 (s, 1 H), 8.93 (s, 1 H), 7.72 (s, 1 H), 7.32 (m, 3 H), 7.22 (m, 4 H), 7.14 (t, 1 H, J=7.8 Hz), 6.77 (d, 1 H, J=7.5 Hz), 6.57 (t, 1 H, J=5.7 Hz) 5.07 (d, 1 H, J=3.3 Hz), 3.55 (m, 2 H), 3.53 (s, 3 H), 3.16 (m, 2 H), 3.00 (m, 4 H), 2.80 (m, 1 H), 2.23 (s, 3 H), 2.05 (m, 2 H), 1.93 (m, 4 H); $^{13}$C NMR (DMSO-d$_6$) δ 165.9, 155.5, 152.1, 148.5, 145.2, 144.3, 140.6, 128.7, 128.6, 126.6, 119.0, 116.6, 115.5, 99.0, 54.0, 52.0, 50.8, 36.5, 25.2, 24.5, 17.9.

Anal. Calcd for $C_{28}H_{35}N_5O_4$.HCl. $H_2O$: C, 60.05; H, 6.84; N, 12.50. Found: C, 60.24; H, 6.57; N, 12.22.

EXAMPLE 4

1,2,3,6-Tetrahydro-1,4-dimethyl-6-(3-nitrophenyl)-2-oxo-5-pyrimidinecarboxylic acid, methyl ester To a stirred solution containing the compound of Formula III obtained from the procedure of Example 1 (7.0 g, 23 mmol) in DMF (50 mL) was added NaH (60% mineral oil dispersion, 1.0 g, 25 mmol), followed by MeI (1.6 mL, 25 mmol). This mixture was stirred 30 min, and then partitioned between $H_2O$ (200 mL) and EtOAc (3×100 mL). The organic extracts were combined, washed with $H_2O$ (2×100 mL), followed by brine (100 mL), and the solvent was removed in vacuo. The resulting 1:1 mixture of 1,6- and 1,4-dihydro-2-methoxypyrimidines was separated by flash chromatography (SiO$_2$: MeOH/CH$_2$Cl$_2$/Hexane), and the identity of these isomers was confirmed by $^1$H NMR after hydrolysis of the methoxy group. Acidic hydrolysis of the 1,6-dihydro isomer (2.42 g, 33% yield) as described for the compound of Example I afforded the title compound as a white solid (2.13 g, 92% yield): mp 217°–219° C.; $^1$H NMR (DMSO-d$_6$) δ 9.59 (s, 1 H), 8.15 (d, 1 H, J=7.8 Hz), 8.09 (s, 1 H), 7.71 (m, 2 H), 5.39 (s, 1 H), 3.53 (s, 3 H), 2.72 (s, 3 H), 2.24 (s, 3 H); $^{13}$C NMR (DMSO-d$_6$) δ 165.3, 151.5, 148.8, 147.9, 144.1, 133.4, 130.4, 122.8, 121.3, 98.7, 60.5, 50.9, 32.3, 17.7.

Anal. Calcd for $C_{14}H_{15}N_3O_5$.0.1 $H_2O$: C, 54.76; H, 4.99; N, 13.68. Found: C, 54.62; H, 4.88; N, 13.65.

EXAMPLE 5

6-(3-Aminophenyl)-1,2,3,6-tetrahydro-1,4-dimethyl-2-oxo-5-pyrimidinecarboxylic acid, methyl ester The title compound was prepared from the compound of Example 4 by the method described in Example 2, using AcOH as solvent. A white solid was obtained in quantitative yield: mp 205°–209° C.; $^1$H NMR (CDCl$_3$): δ 8.69 (s, 1 H), 7.05 (t, 1 H, J=7.8 Hz), 6.69 (d, 1 H, J=7.8 Hz), 6.63 (s,1 H), 6.56 (d, 1 H, J=7.8 Hz),5.10(s, 1 H),3.63 (s,3 H),2.84 (s, 3 H), 2.30 (s, 3 H); $^{13}$C NMR (CDCl$_3$): δ 166.2, 153.2, 146.7, 146.6, 142.5, 129.4, 117.5, 114.8, 113.4, 100.9, 62.3, 51.0, 32.8, 18.6.

Anal. Calcd for $C_{14}H_{17}N_3O_3 \cdot 0.2\ H_2O$ : C, 60.29; H, 6.29; N, 15.07. Found: C, 60.56; H, 6.08; N, 14.81.

EXAMPLE 6

1,2,3,6-Tetrahydro-1,4-dimethyl-2-oxo-6-[3-[[[[3-(4-phenyl-1 -piperidinyl)propyl]amino]carbonyl]amino] phenyl]-5-pyrimidinecarboxylic acid, methyl ester maleate The title compound was prepared from the compound of Example 5 and the intermediate of Formula VII by the method described in Example 3. The solvent was removed in vacuo from the reaction mixture, and the residue partitioned between CH$_2$Cl$_2$ and H$_2$O. The organic extract was dried over Na$_2$SO$_4$, the solvent removed in vacuo, and the residue subjected to flash chromatography (SiO$_2$: MeOH/CH$_2$Cl$_2$). The resulting material was dissolved in a solution of maleic acid in CH$_2$Cl$_2$ to afford the maleate salt as a white solid (15% yield): mp 73°–79° C.; $^1$H NMR (DMSO-d$_6$) δ 9.39 (s, 1 H), 8.69 (s, 1 H), 7.24 (m, 8 H), 6.79 (d, 1 H, J=7.8 Hz), 6.32 (t, 1 H, J=5.7 Hz), 6.06 (s, 2 H), 5.10 (s, 1 H), 3.60 (m, 2 H), 3.53 (s, 3 H), 3.28 (br m, 2 H), 3.16 (m, 4 H), 2.82 (m, 1 H), 2.69 (s, 3 H), 2.21 (s, 3 H), 2.03 (m, 2 H), 1.86 (m, 4 H); $^{13}$C NMR (DMSO-d$_6$) δ 167.2, 165.6, 155.5, 151.7, 147.7, 144.0, 142.2, 140.7, 135.5, 128.8, 128.6, 126.7, 126.5, 119.7, 117.2, 115.9, 99.3, 61.3, 54.1, 52.2, 50.8, 36.5, 32.3, 30.1, 24.9, 17.7.

Anal. Calcd for $C_{29}H_{37}N_5O_4 \cdot 1.25\ C_4H_4O_4 \cdot H_2O$: C, 59.81; H, 6.50; N, 10.26. Found: C, 60.12; H, 6.42; N, 10.00.

EXAMPLE 7

1,2,3,6-Tetrahydro-4-methyl-6-(3-nitrophenyl)-2-oxo-1,5-pyrimidinedicarboxylic acid, dimethyl ester The general method described by Atwal, K. S., et al., *J. Org. Chem.*, (1989) 54, 5898–907, was utilized. A solution of methyl chloroformate (0.26 mL, 4.9 mmol) in CH$_2$Cl$_2$ (5 mL) was added dropwise to a stirred solution containing the compound of Formula III (1.4 g, 4.7 mmol) and pyridine (0.4 mL, 5 mmol) in CH$_2$Cl$_2$ (15 mL) at 0 ° C. The resulting mixture was stirred at room temperature for 30 min, and the solvent removed in vacuo. The residue was partitioned between EtOAc and saturated Na$_2$CO$_3$, then the organic extract was rinsed with water, followed by brine, and the solvent removed in vacuo. A mixture of the desired 1,6-dihydro-2-methoxypyrimidine and the hydrolysis product of the 1,4-isomer precipitated after addition of Et$_2$O. After filtration, hexane was added to the mother liquor, and the 1,6-dihydro-2-methoxypyrimidine was isolated as a white solid (1.06 g, 62% yield). Subsequent acidic hydrolysis of the methoxy group as described for the compound of Example 1 afforded the title compound as a white solid (690 mg, 90% yield): mp 152°–155° C.; $^1$H NMR (DMSO-d$_6$) δ 10.32 (s, 1 H), 8.17 (m, 1 H), 8.04 (s, 1 H), 7.71 (m, 2 H), 6.23 (s, 1 H), 3.78 (s, 3 H), 3.66 (s, 3 H), 2 30 (s, 3 H); $^{13}$C NMR (DMSO-d$_6$) δ 165.0, 153.7, 148.6, 148.3, 148.0, 142.1, 132.8, 130.6, 123.2, 120.7, 102.2, 54.8, 54.3, 51.6, 17.3.

Anal. Calcd for $C_{15}H_{15}N_3O_7$: C, 51.58; H, 4.33; N, 12.03. Found: C, 51.49; H, 4.15; N, 12.07.

EXAMPLE 8

6-(3-Aminophenyl)-1,2,3,6-tetrahydro-4-methyl-2-oxo-1, 5-pyrimidinedicarboxylic acid, dimethyl ester The title compound was prepared from the compound of Example 7 according to the method described in Example 2 using AcOH as solvent. A white solid was obtained (97% yield): mp 190°–193° C.; $^1$H NMR (CDCl$_3$) δ 7.65 (s, 1 H), 7.05 (t, 1 H, J=7.8 Hz), 6.69 (d, 1 H, J=7.8 Hz), 6.64 (s, 1 H), 6.57 (d, 1 H, J=7.8 Hz), 6.30 (s, 1 H), 3.86 (s, 3 H), 3.74 (s, 3 H), 2.36 (s, 3 H); $^{13}$C NMR (CDCl$_3$) δ 165.6, 153.7, 150.1, 146.6, 145.7, 140.6, 129.6, 116.6, 114.9, 113.0, 105.0, 56.0, 54.3, 51.6, 18.1.

Anal. Calcd for $C_{15}H_{17}N_3O_5 \cdot 0.2\ H_2O$: C, 55.79; H, 5.43; N, 13.01. Found: C, 56.02; H, 5.53; N, 12.66.

EXAMPLE 9

1,2,3,6-Tetrahydro-4-methyl-2-oxo-6-[3-[[[[3-(4-phenyl-1-piperidinyl)propyl]amino]carbonyl]amino]phenyl]-1,5-pyrimidinedicarboxylic acid, dimethyl ester The title compound was prepared from the compound of Example 8 and the intermediate of Formula VII, according to the method described in Example 3. The solvent was removed in vacuo from the reaction mixture, and the residue was partitioned between CH$_2$Cl$_2$ and H$_2$O. The organic extract was dried over Na$_2$SO$_4$ and the solvent removed in vacuo. The residue was then subjected to flash chromatography (SiO$_2$: MeOH/CH$_2$Cl$_2$), obtaining a fraction enriched with the desired product. This was dissolved in CH$_2$Cl$_2$, then 1N HCl/Et$_2$O (1.5 mL) was added, and the solvent removed in vacuo. The title compound was isolated by flash chromatography (SiO$_2$: MeOH/CH$_2$Cl$_2$) as a light yellow solid (13% yield): mp 125°–130° C.; $^1$H NMR (DMSO-d$_6$) δ 10.29 (br s, 1 H), 10.15 (s, 1 H), 8.90 (s, 1 H), 7.40 (d, 1 H, J=8.1 Hz), 7.27 (m, 7 H), 6.73 (d, 1 H, J=7.8 Hz), 6.49 (m, 1 H), 6.13 (s, 1 H), 3.75 (s, 3 H), 3.64 (s, 3 H), 3.52 (m, 2 H), 3.16 (m, 2 H), 3.04 (m, 4 H), 2.79 (m, 1 H), 2.27 (s, 3 H), 2.00 (m, 6 H); $^{13}$C NMR (DMSO-d$_6$) δ 165.2, 155.4, 153.7, 148.6, 147.8, 144.3, 140.9, 140.2, 128.9, 128.6, 126.6, 118.4, 117.2, 115.4, 103.0, 54.9, 54.0, 52.0, 51.4, 38.8, 36.5, 30.0, 24.7, 17.1.

Anal. Calcd for $C_{30}H_{37}N_5O_6 \cdot HCl \cdot 1.3\ H_2O$: C, 57.79; H, 6.56; N, 11.23. Found: C, 57.89; H, 6.27; N, 11.20.

EXAMPLE 10

1,2,3,6-Tetrahydro-4-methyl-2-oxo-6-[3-[[[[3-[4-(3-methoxyphenyl)-1-piperidinyl]propyl]amino]carbonyl] amino]phenyl]-1, 5-pyrimidinedicarboxylic acid, dimethyl ester A solution of the compound of Example 8 (1.35 g, 4.23 mmol) and 3-chloropropyl isocyanate (0.5 mL, 5 mmol) in CH$_2$Cl$_2$ (50 mL) was refluxed for 3 h. The solvent was removed in vacuo, and the residue was subjected to flash chromatography (SiO$_2$: 3% MeOH/CH$_2$Cl$_2$) to afford the urea as a pale yellow solid [1.51 g, 82% yield. A mixture of this material (1.3 g, 3.0 mmol), 4-(3-methoxyphenyl) piperidine [prepared by the method of G. A. Loew, et al., *Mol. Pharmacol.*, (1988), 34, 363–376] (600 mg, 3.1 mmol), K$_2$CO$_3$ (850 mg), and NaI (80 mg) in MeCN (75 mL) was refluxed overnight. The reaction mixture was then taken up in water and extracted with CH$_2$Cl$_2$. The organic extract was dried (Na$_2$SO$_4$), and the solvent was removed in vacuo. The residue was then subjected to flash chromatography (SiO$_2$: 7.5–10% MeOH/CH$_2$Cl$_2$) to afford the title compound as a white solid (115 mg, 6% yield): mp 85–°90° C.; MS (IS) m/z 594 (MH$^+$); $^1$H NMR (CDCl$_3$) δ 7.69 (s, 1 H), 7.45 (d, 1 H, J=8.7 Hz), 7.19 (m, 3 H), 6.96 (d, 1 H, J=7.8 Hz), 6.72 (m, 4 H), 6.29 (s, 1 H), 5.83 (m, 1 H), 3.78 (s, 3 H), 3.76 (s, 3 H), 3.70 (s, 3 H), 3.19 (m, 2 H), 3.00 (m, 2 H), 2.40 (m, 3 H), 2.30 (s, 3 H), 2.00 (m, 2 H), 1.76 (m, 2 H), 1.67 (m, 4 H); $^{13}$C NMR (CDCl$_3$) δ 165.7, 159.6, 156.4, 150.2, 147.7, 146.6, 140.5, 139.9, 129.4, 121.3, 119.8, 119.2, 117.2, 112.9, 111.2, 104.9, 56.2, 56.0, 55.1, 54.2, 54.1, 51.6, 42.4, 38.7, 33.0, 26.9, 17.8.

High Resolution Mass Spectrum Calcd for $C_{31}H_{40}N_5O_7$ (MH$^+$): 594.2928. Found: 594.2906.

What is claimed is:

1. A compound of the formula

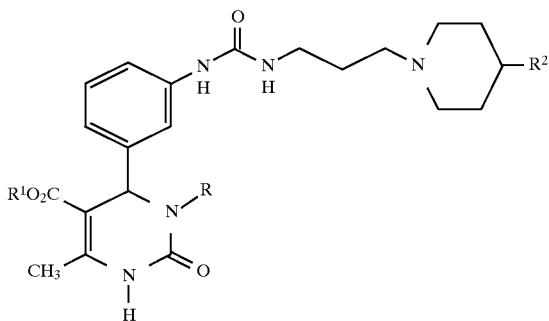

wherein
R is hydrogen, $C_{1-3}$ alkyl or $CO_2R^1$;
$R^1$ is $C_{1-3}$ alkyl; and
$R^2$ is phenyl or methoxyphenyl; or a nontoxic pharmaceutically acceptable salt thereof.

2. A compound of claim 1 wherein R is $CO_2R^1$.

3. A compound of claim 2 wherein $R^1$ is methyl.

4. The compound of claim 1 which is 1,2,3,6-tetrahydro-4-methyl-2-oxo-6-[3-[[[[3-(4-phenyl-1-piperidinyl)propyl]amino]carbonyl]-amino]phenyl]-1,5-pyrimidinedicarboxylic acid, dimethyl ester or a nontoxic pharmaceutically acceptable salt thereof.

5. The compound of claim 1 which is 1,2,3,6-tetrahydro-4-methyl-2-oxo-6-[3-[[[[3-[4-(3-methoxyphenyl)-1-piperidinyl]propyl]amino]carbonyl]-amino]phenyl]-1,5-pyrimidinedicarboxylic acid, dimethyl ester or a nontoxic pharmaceutically acceptable salt thereof.

6. A method of promoting weight loss and treating eating disorders in a mammal which comprises administering to a mammalian host an anorexiant effective dose of a compound claimed in claim 1.

7. A pharmaceutical composition for use in promoting weight loss and treating eating disorders comprising an anorexiant effective amount of a compound claimed in claim 1 in combination with a pharmaceutically acceptable carrier.

* * * * *